US007915207B2

(12) United States Patent
Herdt et al.

(10) Patent No.: US 7,915,207 B2
(45) Date of Patent: Mar. 29, 2011

(54) ANTIMICROBIAL COMPOSITIONS FOR USE ON FOOD PRODUCTS

(75) Inventors: Joy G. Herdt, Hastings, MN (US); Jocelyn H. Chopskie, Eagan, MN (US); Scott L. Burnett, St. Paul, MN (US); Teresa C. Podtburg, Waconia, MN (US); Timothy A. Gutzmann, Eagan, MN (US)

(73) Assignee: Ecolab Inc., St. Paul, MN (US)

( * ) Notice: Subject to any disclaimer, the term of this patent is extended or adjusted under 35 U.S.C. 154(b) by 619 days.

(21) Appl. No.: 11/459,069

(22) Filed: Jul. 21, 2006

(65) Prior Publication Data
US 2007/0020365 A1 Jan. 25, 2007

Related U.S. Application Data

(60) Provisional application No. 60/702,243, filed on Jul. 25, 2005.

(51) Int. Cl.
*C11D 1/83* (2006.01)
(52) U.S. Cl. ..................................... 510/111
(58) Field of Classification Search ................... 510/111
See application file for complete search history.

(56) References Cited

U.S. PATENT DOCUMENTS

| | | | |
|---|---|---|---|
| 2,858,225 A | 10/1958 | Gooding et al. |
| 3,057,735 A | 10/1962 | Ottke et al. |
| 3,443,972 A | 5/1969 | DiMarco et al. |
| 3,867,300 A | 2/1975 | Karabinos et al. |
| 4,002,775 A | 1/1977 | Kabara |
| 4,067,997 A | 1/1978 | Kabara |
| 4,404,040 A | 9/1983 | Wang |
| 4,647,458 A | 3/1987 | Ueno et al. |
| 4,776,974 A | 10/1988 | Stanton et al. |
| 5,208,257 A | 5/1993 | Kabara |
| 5,234,703 A | 8/1993 | Guthery |
| 5,234,719 A | 8/1993 | Richter et al. |
| 5,330,769 A | 7/1994 | McKinzie et al. |
| 5,391,379 A | 2/1995 | McKinzie et al. |
| 5,536,008 A | 7/1996 | Clapper, Jr. |
| 5,573,800 A | 11/1996 | Wilhoit |
| 6,033,705 A | 3/2000 | Isaacs |
| 6,063,425 A | 5/2000 | Kross et al. |
| 6,113,963 A | 9/2000 | Gutzmann et al. |
| 6,136,769 A | 10/2000 | Asano et al. |
| 6,183,807 B1 | 2/2001 | Gutzmann et al. |
| 6,187,348 B1 | 2/2001 | Polster |
| 6,262,038 B1 | 7/2001 | Pierce et al. |
| 6,472,358 B1 | 10/2002 | Richter et al. |
| 6,500,861 B1 | 12/2002 | Wider |
| 6,509,050 B1 | 1/2003 | Henson et al. |
| 6,528,101 B1 | 3/2003 | Polster |
| 6,559,189 B2 | 5/2003 | Baker, Jr. et al. |
| 6,579,556 B2 | 6/2003 | Kirby et al. |
| 6,586,026 B1 | 7/2003 | Ramesh et al. |
| 6,613,364 B2 | 9/2003 | Begg et al. |
| 6,620,446 B2 | 9/2003 | King et al. |
| 6,638,978 B1 | 10/2003 | Kabara |
| 6,767,569 B1 | 7/2004 | Marsden et al. |
| 6,843,043 B2 | 1/2005 | Hanson et al. |
| 6,976,347 B2 | 12/2005 | Karman et al. |
| 7,090,882 B2 | 8/2006 | Koefod et al. |
| 2002/0064585 A1 | 5/2002 | Christianson et al. |
| 2002/0164405 A1 | 11/2002 | Polster |
| 2002/0192340 A1 | 12/2002 | Swart et al. |
| 2002/0197366 A1 | 12/2002 | King et al. |
| 2003/0039632 A1 | 2/2003 | Stiles et al. |
| 2003/0047087 A1 | 3/2003 | Phebus et al. |
| 2003/0099745 A1 | 5/2003 | Grinstead et al. |
| 2003/0228401 A1 | 12/2003 | Newman et al. |
| 2004/0013694 A1 | 1/2004 | Newman et al. |
| 2004/0018283 A1 | 1/2004 | Hirschey et al. |
| 2004/0018284 A1 | 1/2004 | Kuethe et al. |
| 2004/0033296 A1 | 2/2004 | Yuan et al. |
| 2004/0043922 A1 | 3/2004 | Naidu |
| 2004/0050020 A1 | 3/2004 | Hanson et al. |
| 2004/0058041 A1 | 3/2004 | Greenwald |
| 2004/0105927 A1 | 6/2004 | Karman et al. |
| 2004/0131709 A1 | 7/2004 | Berdahl et al. |
| 2004/0146619 A1 | 7/2004 | Maye |
| 2004/0166216 A1 | 8/2004 | Marsden et al. |
| 2004/0175480 A1 | 9/2004 | Seman et al. |
| 2005/0022468 A1 | 2/2005 | Hanson et al. |
| 2005/0032668 A1 | 2/2005 | Pedersen et al. |
| 2005/0152991 A1 | 7/2005 | Man et al. |
| 2005/0159324 A1 | 7/2005 | Man et al. |

(Continued)

FOREIGN PATENT DOCUMENTS

EP 0128610 12/1984

(Continued)

OTHER PUBLICATIONS

Juneja V.K. et al., "Control of *Clostridium perfringens* in a model roast beef by salts of organic acids during chilling", Journal of Food Safety, vol. 24, No. 2, 2004, pp. 95-108, XP008071343, ISSN: 0149-6085.

McCormick K E. et al., "In-package pasteurization combined with biocide-impregnated films to inhibit *Listeria monocytogenes* and *Salmonella typhimurium* in turkey bologna." Journal of Food Science, vol. 70, No. 1, Jan. 2005, pp. M52-M57, XP008071365.

Samelis J et al., "Control of *Listeria monocytogenes* with combined antimicrobials after postprocess contamination and extended storage of frankfurters at 4 degree C in vacuum packages." Journal of Food Protection, vol. 65, No. 2, 2002, pp. 299-307, XP008071340.

Chen, Sebranek, Dickson & Mendonca, "*Combining Pediocin (ALTA 2341) with Postpackaging Thermal Pasteurization for Control of Listeria monocytogenes on Frankfurters*", Journal of Food Protection, vol. 67, No. 9, 2004, pp. 1855-1865, 11 pgs.

(Continued)

*Primary Examiner* — John R Hardee
(74) *Attorney, Agent, or Firm* — Merchant & Gould P.C.

(57) ABSTRACT

The present invention relates to antimicrobial compositions, and specifically antimicrobial compositions that are useful at sanitizing food products. The compositions of the present invention include octanoic acid, an acidulant, a coupling agent, an optional buffer, and water. The compositions of the present invention are composed of GRAS or food additive raw materials.

8 Claims, No Drawings

U.S. PATENT DOCUMENTS

| | | | |
|---|---|---|---|
| 2006/0286229 | A1 | 12/2006 | Koefod et al. |
| 2007/0020366 | A1 | 1/2007 | Luchansky et al. |

FOREIGN PATENT DOCUMENTS

| | | |
|---|---|---|
| EP | 0750853 | 1/1997 |
| EP | 0940090 | 9/1999 |
| EP | 1561801 | 8/2005 |
| EP | 1621085 | 2/2006 |
| JP | 06054672 | 3/1994 |
| WO | WO01/05254 | 1/2001 |
| WO | WO01/49121 | 7/2001 |
| WO | WO02/054866 | 7/2002 |
| WO | WO02/060280 | 8/2002 |
| WO | WO03/073849 | 9/2003 |
| WO | WO2004/057984 | 7/2004 |

OTHER PUBLICATIONS

Gombas, D, Chen, Y., Clavero, R., and Scott, V., "*Survey of Listeria monocytogenes in Ready-to-Eat Foods*", National Food Journal of Food Protection, vol. 66, No. 4, 2003, pp. 559-569, 11 pgs.

Luchansky, J.B., "*Viability of Listeria monocytogenes on Commercially-prepared Hams Surface Treated with Acidic Calcium Sulfate and Lauric Arginate and Stored at 4° C*", Meat Science 71 (2005), pp. 92-99.

McCormick, K.E. et al. "*In-Package Pasteurization Combined with Biocide-Impregnated Films to Inhibit Listeria monocytogenes and Salmonella typhimurium in Turkey Bologna*", Journal of Food Science, Institute of Food Technologists, Chicago, IL, U.S., vol. 70, No. 1, Jan. 11, 2005, pp. M52-M57, XP008071365 ISSN: 0022-1147.

Samelis, J. et al., "*Control of Listeria monocytogenes with Combined Antimicrobials after Postprocess Contamination and Extended Storage of Frankfurters at 4° C in Vacuum Packages*", Journal of Food Protection, Des Moines, IO, U.S., vol. 65, No. 2, Jan. 1, 2002, pp. 299-307, XP008071340, ISSN: 0362-028X.

Ababouch, L., Chaibi, A., Busta, F.F., Inhibition of Bacterial Spore Growth by Fatty Acids and Their Sodium Salts, Journal of Food Protection, vol. 55, No. 12, Dec. 1992, pp. 980-984, International Association for Food Protection.

Ariyapitipun, Tipayanate; Mustapha, Azlin; Clarke, Andrew D., "Survival of *Listeria monocytogenes* Scott A on Vacuum-Packaged Raw Beef Treated with Polylactic Acid, Lactic Acid, and Nisin", Journal of Food Protection, vol. 63, No. 1, Jan. 2000, pp. 131-136(6), International Association for Food Protection.

Bedie G.K.; Samelis J.; Sofos J.N.; Belk K.E.; Scanga J.A.; Smith G.C., "Antimicrobials in the Formulation to Control *Listeria monocytogenes* Postprocessing Contamination on Frankfurters Stored at 4° C in Vacuum Packages", Journal of Food Protection, vol. 64, No. 12, Dec. 1, 2001, pp. 1949-1955(7), International Association for Food Protection.

Bedie G.K.; Kain, M.L. Samelis, J., Sofos, J.N. Belk K.E.; Scanga J.A.; Smith G.C., "Evaluation of Antimicrobial Incorporated into the Formulation Against Post-Processing Contamination of *Listeria monocytogenes* on Frankfurters Stored at 4° C in Vacuum Packages", 2001 Animal Sciences Research Report, the Department of Animal Sciences, Colorado State University, pp. 1-5.

Blaszyk, M., Holley, R.A., "Interaction of monolaurin, eugenol and sodium citrate on growth of common meat spoilage and pathogenic organisms", International Journal of Food Microbiology 39 (1998) pp. 175-183.

C.-M. Chen; J.G. Sebranek; J.S. Dickson; A.F. Mendonca, "Combining Pediocin with Postpackaging Irradiation for Control of *Listeria monocytogenes* on Frankfurters", Journal of Food Protection, vol. 67, No. 9, Sep. 1, 2004, pp. 1866-1875(10), International Association for Food Protection.

Calicioglu M.; Kaspar C.W.; Buege D.R.; Luchansky J.B., "Effectiveness of Spraying with Tween 20 and Lactic Acid in Decontaminating Inoculated *Escherichia coli* O157:H7 and Indigenous *Escherichia coli* Biotype I on Beef", Journal of Food Protection, vol. 65, No. 1, Jan. 1, 2002, pp. 26-32(7), International Association for Food Protection.

Chen, C., Sebranek, JG., Dickson, J.S., Mendonca, A.F., "Use of Pediocin (Alta™ 2341) for Control of *Listeria monocytogenes* on Frankfurters", Journal of Muscle Foods, vol. 15, pp. 35-56.

Davies, E. Alison; Milne, Catherine F.; Bevis, Helen E.; Potter, Richard W.; Harris, Jo M.; Williams, Graham C.; Thomas, Linda V.; Delves-Broughton, Joss, "Effective Use of Nisin to Control Lactic Acid Bacterial Spoilage in Vacuum-Packed Bologna-type Sausage", Journal of Food Protection, vol. 62, No. 9, Sep. 1999, pp. 1004-1010(7), International Association for Food Protection.

Farid, M., Bal'A, A., Marshall, D.L., "Organic Acid Dipping of Catfish Fillets: Effect on Color, Microbial Load, and *Listeria monocytogenes*", Journal of Food Protection, vol. 61, No. 11, 1998, pp. 1470-1474, International Association for Food Protection.

Friedman M.; Henika P.R.; Mandrell R.E., "Antibacterial Activities of Phenolic Benzaldehydes and Benzoic Acids against *Campylobacter jejuni, Escherichia coli, Listeria monocytogenes*, and *Salmonella enterica*", Journal of Food Protection, vol. 66, No. 10, Oct. 1, 2003, pp. 1811-1821(11), International Association for Food Protection.

Friedman M.; Henika P.R.; Mandrell R.E., "Bactericidal Activities of Plant Essential Oils and Some of Their Isolated Constituents against *Campylobacter jejuni, Escherichia coli, Listeria monocytogenes*, and *Salmonella enterica*", Journal of Food Protection, vol. 65, No. 10, Oct. 1, 2002, pp. 1545-1560(16), International Association for Food Protection.

Gande N.; Muriana P., "Prepackage Surface Pasteurization of Ready-to-Eat Meats with a Radiant Heat Oven for Reduction of *Listeria monocytogenes*", Journal of Food Protection, vol. 66, No. 9, Sep. 1, 2003, pp. 1623-1630(8), International Association for Food Protection.

Glass K.A.; Granberg D.A.; Smith A.L.; McNamara A.M.; Hardin M.; Mattias J.; Ladwig K.; Johnson E.A., "Inhibition of *Listeria monocytogenes* by Sodium Diacetate and Sodium Lactate on Wieners and Cooked Bratwurst", Journal of Food Protection, vol. 65, No. 1, Jan. 1, 2002, pp. 116-123(8), International Association for Food Protection.

Islam M.; Chen J.; Doyle M.P.; Chinnan M., "Control of *Listeria monocytogenes* on Turkey Frankfurters by Generally-Recognized-as-Safe Preservatives", Journal of Food Protection, vol. 65, No. 9, Sep. 1, 2002, pp. 1411-1416(6), International Association for Food Protection.

Islam M.; Chen J.; Doyle M.P.; Chinnan M., "Effect of Selected Generally Recognized as Safe Preservative Sprays on Growth of *Listeria monocytogenes* on Chicken Luncheon Meat", Journal of Food Protection, vol. 65, No. 5, May 1, 2002, pp. 794-798(5), International Association for Food Protection.

J.B. Luchansky, J.E. Call, B. Hristova, L. Rumery, L. Yoder and A. Oser, "Viability of *Listeria monocytogenes* on commercially-prepared hams surface treated with acidic calcium sulfate and lauric arginate and stored at 4° C", Meat Science, vol. 71, Issue 1, Sep. 2005, pp. 92-99.

McEntire J.C.; Montville T.J.; Chikindas M.L., "Synergy between Nisin and Select Lactates against *Listeria monocytogenes* Is Due to the Metal Cations", Journal of Food Protection, vol. 66, No. 9, Sep. 1, 2003, pp. 1631-1636(6), International Association for Food Protection.

Muriana P.M.; Quimby W.; Davidson C.A.; Grooms J., "Postpackage Pasteurization of Ready-to-Eat Deli Meats by Submersion Heating for Reduction of *Listeria monocytogenes*", Journal of Food Protection, vol. 65, No. 6, Jun. 1, 2002, pp. 963-969(7), International Association for Food Protection.

Muriana, P, Escoubas, J. R., "Pre- and Post-package Pasteurization of RTE Meats for Reduction of *Listeria monocytogenes*", Oklahoma State University, AMI Foundation, Feb. 2004, 4 pages.

Murphy R.Y.; Berrang M.E., "Thermal Lethality of *Salmonella* Senftenberg and *Listeria innocua* on Fully Cooked and Vacuum Packaged Chicken Breast Strips during Hot Water Pasteurization", Journal of Food Protection, vol. 65, No. 10, Oct. 1, 2002, pp. 1561-1564(4), International Association for Food Protection.

Murphy R.Y.; Duncan L.K.; Driscoll K.H.; Beard B.L.; Berrang M.B.; Marcy J.A. "Determination of Thermal Lethality of *Listeria monocytogenes* in Fully Cooked Chicken Breast Fillets and Strips during Postcook In-Package Pasteurization", Journal of Food Protection, vol. 66, No. 4, Apr. 1, 2003, pp. 578-583(6), International Association for Food Protection.

Murphy R.Y.; Duncan L.K.; Driscoll K.H.; Marcy J.A.; Beard B.L., "Thermal Inactivation of *Listeria monocytogenes* on Ready-to-Eat Turkey Breast Meat Products during Postcook In-Package Pasteurization with Hot Water", Source: Journal of Food Protection, vol. 66, No. 9, Sep. 1, 2003, pp. 1618-1622(5), International Association for Food Protection.

Nykanen, A., Weckman, K., Lapvetelainen, A., "Synergistic inhibition of *Listeria monocytogenes* on cold-smoked rainbow trout by nisin and sodium lactate", International Journal of Food Microbiology, vol. 61 (2000), pp. 63-72.

Porto A.C.S.; Call J.E.; Luchansky J.B., "Effect of Reheating on Viability of a Five-Strain Mixture of *Listeria monocytogenes* in Vacuum-Sealed Packages of Frankfurters following Refrigerated or Frozen Storage", Journal of Food Protection, vol. 67, No. 1, Jan. 1, 2004, pp. 71-76(6), International Association for Food Protection.

Samelis J.; Bedie G.K.; Sofos J.N.; Belk K.E.; Scanga J.A.; Smith G.C., "Control of *Listeria monocytogenes* with Combined Antimicrobials after Postprocess Contamination and Extended Storage of Frankfurters at 4° C in Vacuum Packages", Journal of Food Protection, vol. 65, No. 2, Feb. 1, 2002, pp. 299-307(9), International Association for Food Protection.

Samelis J.; Sofos J.N.; Kain M.L.; Scanga J.A.; Belk K.E.; Smith G.C., "Organic Acids and Their Salts as Dipping Solutions to Control *Listeria monocytogenes* Inoculated following Processing of Sliced Pork Bologna Stored at 4° C in Vacuum Packages", Journal of Food Protection, vol. 64, No. 11, Nov. 1, 2001, pp. 1722-1729(8), International Association for Food Protection.

Vermeiren, L., Devlieghere, F., Debevere, J., "Effectiveness of some recent antimicrobial packaging concepts", Food Additives and Contaminants, 2002, vol. 19, Supplement, 163-171.

Yen, L.C., Sofos, J.N., Schmidt, G.R., "Effect of Meat Curing Ingredients on Thermal Destruction of *Listeria monocytogenes* in Ground Pork", Journal of Food Protection. vol. 54, pp. 408-412, International Association for Food Protection.

Zeitoun, A.A.M., Debevere, J.M., "Inhibition, survival and growth of *Listeria monocytogenes* on poultry as influenced by buffered lactic acid treatment and modified atmosphere packaging", International Journal of Food Microbiology, vol. 14 (1991), pp. 161-170.

ANTIMICROBIAL COMPOSITIONS FOR USE ON FOOD PRODUCTS

CROSS REFERENCE TO RELATED APPLICATION

This application claims priority under 35 U.S.C. §119(e) to U.S. Provisional Application entitled "ANTIMICROBIAL COMPOSITIONS FOR USE ON FOOD PRODUCTS", Ser. No. 60/702,243, filed on Jul. 25, 2005, which is incorporated herein by reference in its entirety. This application is related to subject matter disclosed in U.S. patent application for "ANTIMICROBIAL COMPOSITIONS AND METHODS FOR TREATING PACKAGED FOOD PRODUCTS", Ser. No. 11/459,067, filed concurrently herewith, the subject matter of which is incorporated in this application by reference.

FIELD OF THE INVENTION

The present invention relates to antimicrobial compositions, and specifically antimicrobial compositions that are useful at sanitizing food products. The compositions of the present invention include octanoic acid, an acidulant, a coupling agent, an optional buffer, and water. The compositions of the present invention are composed of GRAS or food additive raw materials.

BACKGROUND

During the processing, preparation and packaging of food products, the food product may encounter microorganisms which may make the food unsuitable for consumption. The microorganisms may come from the food itself, the food contact surfaces, and/or the surrounding environment. The microorganisms can range from pathogenic microorganisms (e.g., *Listeria monocytogenes*, enterohemorrhagic *Escherichia coli, Salmonella* and the like) to spoilage organisms that can affect the taste, color, and/or smell of the final food product (e.g., *Pseudomonas, Acinetobacter, Moraxella, Alcaligenes, Flavobacterium, Erwinia*, and the like). Microorganisms can affect a wide variety of food products including meat, poultry, fish and shellfish, cheese, fruits and vegetables, and pre-prepared foods. At certain levels, the presence of microorganisms on a food product may cause everything from a consumer's perception of a lower quality product, to regulatory investigations and sanctions, to foodbourne illness and death.

Food processors use a variety of methods during processing to control and/or reduce the presence of microorganisms on food products. These methods include everything from cleaning and sanitizing the food processing plant environment, applying or incorporating antimicrobials to or in the food product, irradiating the food product, applying heat, and others. Applying or incorporating an antimicrobial composition to or in the food product is a preferred way of controlling microorganisms. However, it is difficult to formulate a composition that is effective at reducing microorganisms using ingredients that are acceptable for direct food contact according to government regulations. Further, it is difficult to formulate a composition that can be applied directly to a food product without adversely affecting the color, taste, or smell of the food product. Finally, once a food product has been treated with an antimicrobial composition or process to control the presence of microorganisms on the food product, the opportunity exists for the food product to become re-contaminated during further processing.

Food safety agencies have issued guidelines for processing food that may have exposure to surfaces contaminated with microorganisms including *Listeria monocytogenes, Salmonella*, and *E. coli* O157-H7. See e.g., Food Safety Inspection Service (FSIS) final rule for the control of *Listeria monocytogenes* in ready-to-eat (RTE) meat and poultry products, 9 CFR 430.

The FSIS guidelines on *Listeria* provide three alternatives for controlling the presence of *Listeria* on a RTE product. Under Alternative 1, an establishment applies a post-lethality treatment to the RTE product and an antimicrobial agent or process to control or suppress the growth of *L. monocytogenes* during the shelf life of the RTE product. Under Alternative 2, an establishment applies either a post-lethality treatment or an antimicrobial agent or process to suppress the growth of *L. monocytogenes*. Under Alternative 3, an establishment does not apply any post-lethality treatment or antimicrobial agent or process. Instead, it relies on its sanitation program to prevent the presence of *L. monocytogenes*. RTE products produced under Alternative 2 have greater control over potential *Listeria* contamination than RTE products produced under Alternative 3. Similarly, RTE products produced under Alternative 1 have greater control over *Listeria* contamination than those produced under Alternative 2. Besides providing better microbial control for RTE products, facilities operating under Alternative 1 are subject to less agency intervention (e.g., inspections, recordkeeping, etc.) than an Alternative 2 or Alternative 3 facility.

*Salmonella* is known to be prevalent on raw poultry, beef, and pork. Further, *Salmonella* has a high incidence of causing foodbourne illness, and sometimes severe foodbourne illness. Establishments must employ processes validated to achieve specific levels of reduction of *Salmonella* organisms throughout their finished RTE meat and poultry product (6.5 $\log_{10}$ throughout finished meat products and 7 $\log_{10}$ throughout finished poultry products).

*E. coli* O157:H7 has been linked to foodbourne illness outbreaks. The FSIS has additional lethality performance standards for all fermented RTE products that include any amount of beef, except thermally-processed, commercially sterile products. Establishments must employ processes validated to achieve a 5.0 $\log_{10}$ reduction of *E. coli* O157:H7 throughout fermented products containing beef.

It is against this background that the present invention has been made.

SUMMARY

Surprisingly, it has been discovered that microorganisms on food products can be reduced by applying the antimicrobial composition of the present invention to the food product. The antimicrobial compositions of the present invention include octanoic acid, an acidulant, a coupling agent, an optional buffer, and water. The antimicrobial compositions of the present invention are preferably composed of food grade or GRAS ingredients which are advantageous because they have been previously demonstrated as safe and they can be applied to sensitive surfaces such as food products without having to be rinsed off afterwards. Application of an antimicrobial composition on a food product is a preferred method of effectively reducing the presence of microorganisms on the food product. Also, not having a water rinse eliminates the potential for recontamination during a water rinse and the presence of a wet environment for microorganisms to grow in. Further, when used in certain methods, the antimicrobial composition can remain on the food product and continue to provide an antimicrobial effect for an extended period of time. For example, the antimicrobial composition may continue to provide an antimicrobial effect until just after the food product has been packaged, or throughout the shelf life of the food product.

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

DETAILED DESCRIPTION OF SOME EMBODIMENTS

The present invention relates to antimicrobial compositions, and specifically antimicrobial compositions that are useful at sanitizing food products. The compositions of the present invention include octanoic acid, an acidulant, a coupling agent, an optional buffer, and water. The compositions of the present invention are composed of GRAS or food additive raw materials.

It is understood that the various embodiments of the present invention described herein may be combined to create a variety of unique embodiments and still remain within the scope of the present invention. Further, it is understood that the examples described herein may be used in conjunction with any of the embodiments described, unless stated otherwise.

Definitions

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The use of the terms "antimicrobial" in this application does not mean that any resulting products are approved for use as an antimicrobial agent.

Antimicrobial Composition

The present invention generally relates to antimicrobial compositions, and specifically antimicrobial compositions that are useful at sanitizing food products. The compositions of the present invention include octanoic acid, an acidulant, a coupling agent, an optional buffer, and water. The compositions of the present invention are preferably formed using GRAS or food additive raw materials.

The antimicrobial compositions of the present invention may be formulated as a concentrate or a ready-to-use composition. A concentrate refers to the composition that is diluted to form the ready-to-use composition. The ready-to-use composition refers to the composition that is applied to a surface. A concentrate may be advantageous because it is less expensive to ship than a ready-to-use composition and it takes up less storage space. The concentrate may then be diluted to form a ready-to-use composition prior to application of the ready-to-use composition.

The antimicrobial composition may have a range of physical forms. For example, the antimicrobial composition may be a solid, liquid, structured or thickened liquid or gel, foam, pellet, prill, or a powder. Further, the antimicrobial composition may be a part of a dissolvable film such as polyvinylalcohol (PVA) or cellulose film, or the antimicrobial composition may be blown or extruded with a film, impregnated in a film, or coated on a film. Finally, the antimicrobial composition may be part of the packaging that is applied to the food product.

Octanoic Acid

The antimicrobial composition includes a $C_6$ to $C_{22}$ fatty acid and in particular octanoic acid as the active antimicrobial agent. Not only does octanoic acid provide the antimicrobial activity, but it is also considered to be "food grade" by the Food Chemicals Codex and a "food additive" by the United States Food and Drug Administration. This combination of antimicrobial activity with direct food application makes octanoic acid particularly useful for applications on food surfaces.

Octanoic acid has the following chemical structure:

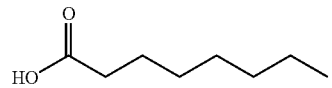

The octanoic acid may be octanoic acid or a derivative thereof. For example, esters of octanoic acid, or salts of octanoic acid may also be used as the active antimicrobial agent. Common ester derivatives of carboxylic acids are those where the hydroxy group is replaced by an alkoxy group which may comprise any number of different alkyl moieties which do not impede the efficacy of the octaonic acid compound.

The principle types of esters result from reaction with monohydric alcohols, polyhydric alcohols, and ethylene or propylene oxide. The most common monohydric alcohols used are the simple alkyl alcohols such as methyl, ethyl, propyl, butyl, isopropyl, and the like. The most common polyhydric alcohols include polyethylene glycol, glycerol, sorbitol, and certain carbohydrates such as sucrose.

Octanoic acid may take the form of a salt by reaction with an alkaline substance most commonly from oxides, hydroxides, or carbonates of monovalent and divalent metals in Periodic Groups IA and IIA but also with basic positive complexes such as the ammonium radical and organic amine moieties.

Accordingly, the octanoic acid of the invention may comprise any number of acid salts, esters, and the like. Preferably, the compound used in the invention is octanoic acid, an octanoic acid salt, an octanoic acid ester, or mixtures thereof.

In some embodiments, the composition can consist essentially of octanoic acid, acidulant, and coupling agent where the composition does not include any additional antimicrobial agents. In some embodiments, the composition can consist of octanoic acid, acidulant, and coupling agent.

When the composition is formulated as a concentrate composition, the octanoic acid may be present in a concentration ranging generally from about 1 wt. % to about 50 wt. %, from about 2 wt. % to about 25 wt. %, and from about 3 wt. % to about 15 wt. %. When the composition is formulated as a ready-to-use composition, the octanoic acid may be present in a concentration ranging generally from about 0.01 wt. % to about 15 wt. %, from about 0.05 wt. % to about 10 wt. %, and from about 0.1 wt. % to about 5 wt. %.

Acidulant

The antimicrobial composition includes one or more acidulants for controlling the pH of the composition. The acidulants used in the present invention are preferably considered GRAS or food additive raw materials. Some non-limiting examples of suitable GRAS or food additive acidulants include lactic acid, phosphoric acid, sulfuric acid, adipic acid, tartaric acid, succinic acid, acetic acid, propionic acid, citric acid, malic acid, sodium acid sulfate, and mixtures thereof. The acidulant is preferably phosphoric acid or citric acid.

The exact amount of the acidulant in the composition will depend on the selection of the acidulant and the strength of the acidulant. The acidulant is preferably included in an amount to provide a desired pH. The pH of the ready-to-use composition is preferably from about 1.0 to about 5.6, from about 1.5 to about 4.5, and from about 2.0 to about 4.0. A person of ordinary skill in the art will be able to determine the weight percentage of acidulant, in equilibrium, necessary to achieve the desired pH. However, exemplary weight percent ranges for the acidulant at equilibrium when the composition is formulated as a concentrate composition range generally from about 1 wt. % to about 50 wt. %, from about 1.5 wt. % to about 25 wt. %, and from about 2 wt. % to about 15 wt. %. When the composition is formulated as a ready-to-use composition, the acidulant may be present at equilibrium in a concentration ranging generally from about 0.1 wt. % to about 15 wt. %, from about 0.2 wt. % to about 10 wt. %, and from about 0.4 wt. % to about 5 wt. %.

Buffers

The antimicrobial composition optionally includes one or more buffers. The buffer is preferably the conjugate base of the acidulant used in the composition. Further, the buffer is preferably considered to be a GRAS or food additive raw material. The buffer can be added directly to the composition in the form of the salt of the acidulant or formed by adding a neutralizing base to the acidulant. For example, if the buffer is created in the composition then a neutralizing base should be added to the acidulant to form the corresponding buffering salt. The neutralizing base is preferably considered GRAS or food additive. Some non-limiting examples of suitable neutralizing bases include sodium hydroxide, potassium hydroxide, silicates, trisodiumphosphates and the like.

The buffer salts are preferably GRAS or food additive. Some non-limiting examples of suitable buffers include citric acid combined with sodium or potassium citrate, or phosphoric acid combined with monosodium phosphate, however, a person skilled in the art will be able to select the corresponding salt of the desired acidulant.

The buffer is preferably citric acid combined with sodium or potassium citrate.

The exact amount of the buffer in the composition will depend on the strength and amount of the acidulant and a person of ordinary skill in the art will be able to determine the exact weight percent of the buffer at equilibrium. However, when the composition is formulated as a concentrate composition, the buffer may be present in a concentration ranging generally from about 1 wt. % to about 50 wt. %, from about 1.5 wt. % to about 25 wt. %, and from about 2 wt. % to about 15 wt. %. When the composition is formulated as a ready-to-use composition, the buffer may be present in a concentration ranging generally from about 0.1 wt. % to about 10.0 wt. %, from about 0.2 wt. % to about 5.0 wt. %, and from about 0.4 wt. % to about 3.0 wt. %. The buffer is preferably included in the composition in an amount effective to maintain the pH of the ready-to-use composition from about 1.0 to about 5.6, from about 1.5 to about 4.5, and from about 2.0 to about 4.0.

Coupling Agents

The antimicrobial composition includes one or more coupling agents for maintaining the raw materials of the composition in solution. The coupling agent is preferably a GRAS or food additive raw material. Some non-limiting examples of suitable coupling agents include propylene glycol esters, glycerol esters, polyoxyethylene glycerol esters, polyglycerol esters, sorbitan esters, polyoxyethylene sorbitan esters, polyoxyethylene-polyoxypropylene polymers, sulfonates, dioctyl sodium succinate, stearoyl lactylate, and complex esters such as acetylated, lactylated, citrated, succinhylated, or diacetyl tartarated glycerides. The coupling agent is preferably a sorbitan ester such as polyoxyethylene (20) sorbitan monooleate, commercially available as Polysorbate 80, polyoxyethylene (20) sorbitan monostearate, commercially available as Polysorbate 60, and polyoxyethylene (20) sorbitan monolaurate, commercially available as Polysorbate 20.

When the composition is formulated as a concentrate composition, the coupling agent may be present in a concentration ranging generally from about 1 wt. % to about 50 wt. %, from about 2 wt. % to about 25 wt. %, and from about 3 wt. % to about 15 wt. %. When the composition is formulated as a ready-to-use composition, the coupling agent may be present in a concentration ranging generally from about 0.02 wt. % to about 15 wt. %, from about 0.05 wt. % to about 10 wt. %, and from about 0.1 wt. % to about 5 wt. %.

Additional Functional Ingredients

The antimicrobial composition may include additional functional ingredients that enhance the effectiveness of the composition or provide some other benefit. Examples of additional functional ingredients that may be included include long chain saturated or unsaturated fatty acids (e.g., $C_6$ to $C_{22}$), oxidizers, carriers, chelating agents, hydrotropes, thickening and/or gelling agents, foaming agents, film-forming agents, surfactants, coupling agents, acidulants, potentiators, flavoring aids, fragrance, dye, and the like. Any additional functional ingredient is preferably a GRAS or food grade ingredient.

Long Chain Fatty Acids

The composition may optionally include a long chain fatty acid, and specifically a $C_6$ to $C_{22}$ fatty acid. Fatty acids are comprised of alkyl groups with 6 to 22 carbon atoms with a terminal carboxylic group (—COOH). Fatty acids may be saturated in which all of the alkyl chain carbon atoms are connected by a single bond. Fatty acids can also be unsaturated where there are one or more double bonds between the carbon atoms. Non-limiting examples of saturated fatty acids include hexanoic ($C_6$), octanoic ($C_8$), nonanoic ($C_9$), decanoic ($C_{10}$), lauric ($C_{12}$), myristic ($C_{14}$), palmitic ($C_{16}$), stearic ($C_{18}$), arachidic ($C_{20}$), behenic ($C_{22}$) and the like. Non-limiting examples of unsaturated fatty acids include palmitoleic ($C_{16:1}$), oleic ($C_{18:1}$), linoleic ($C_{18:2}$), linolenic ($C_{18:3}$), arachidonic ($C_{20:1}$) and the like.

Oxidizers

The composition may optionally include an oxidizer. Some non-limiting examples of oxidizers include peroxygen compounds such as organic and inorganic peroxides, peracids, peresters, and mixtures thereof. Non-limiting examples of inorganic peroxides include: hydrogen peroxide, its salts, and other inorganic acids or salts of percarbonates, persulfates, and perborates. Non-limiting examples of organic peroxides include: benzoyl peroxide, tert-butyl benzoyl peroxide, and other alkyl and/or aryl peroxides. Non-limiting examples of peracids include: performic acid, peracetic acid, perlactic acid, perglycolic acid, chloroperbenzoic acid, perheptanoic acid, peroctanoic acid, perdecanoic acid, percitric acid, perbenzoic acid. Non-limiting examples of perester peracids include: monoester peracids derived from diacids or monoester diacids or diesters (e.g., such as adipic, succinic, glutaric, sebacic, or malonic acids/esters and mixtures thereof).

It is also possible to utilize oxidants capable of generating active oxidizing or oxygen species; including oxygen, ozone, chlorine dioxide, and mixtures thereof. The preferred oxidants are peroxygen compounds including, hydrogen peroxide and inorganic peroxides.

Carriers

The composition may optionally include a carrier or solvent. The carrier may be water or other solvent such as an alcohol or polyol. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g. propylene glycol, ethylene glycol, glycerine, and 1,2-propanediol) can also be used.

Chelating Agents

The compositions of the invention may optionally contain a polyvalent metal complexing or chelating agent that aids in reducing the harmful effects of hardness components and service water and improves product stability. The chelating agent or sequestering agent can effectively complex and remove such ions from inappropriate interaction with active ingredients thus increasing sanitizing agent performance. Both organic and inorganic chelating agents may be used. Inorganic chelating agents include such compounds as sodium tripolyphosphate and other higher linear and cyclic polyphosphate species. Organic chelating agents include both polymeric and small molecule chelating agents. Polymeric chelating agents commonly comprise polyanionic compositions such as polyacrylic acid compounds. Amino phosphates and phosphonates are also suitable for use as chelating agents in the compositions of the invention and include ethylene diamine (tetramethylene phosphonates), nitrilotrismethylene phosphates, diethylenetriamine (pentamethylene phosphonates). These amino phosphates commonly contain alkyl or alkaline groups with less than 8 carbon atoms.

Preferred chelating agents for use in this invention include improved food additive chelating agents such as disodium salts of ethylene diamine tetraacetic acid or the well known phosphonates sold in the form of DEQUEST® materials, for example, 1-hydroxyethylidene-1,1-diphosphonic acid, etc. The phosphonic acid may also comprise a low molecular weight phosphonopolycarboxylic acid such as one having about 24 carboxylic acid moieties and about 1-3 phosphonic acid groups.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

Thickening Agents and Gelling Agents

The composition may optionally include a thickening agent or a gelling agent. Thickeners useful in the present invention are those which do not leave contaminating residue on the surface of application, i.e., constituents which are incompatible with food or other sensitive products in contact areas.

Generally, thickeners which may be used in the present invention include natural gums such as xanthan gum. Also useful in the present invention are cellulosic polymers, such as carboxymethyl cellulose. Generally, the concentration of thickener use in the present invention will be dictated by the desired viscosity within the final composition.

Foaming Agents

The composition may optionally include a foaming agent or foaming surfactant. Foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides.

Film-Forming Agents

The composition of the invention may also contain one or more rheology modifiers, to enhance viscosity, or thicken and cause the aqueous treatment to cling to the surface being treated. Clinging enables the composition to remain in contact with the transient and resident pathogenic bacteria for longer periods of time, thereby promoting microbiological efficacy and resisting waste because of excessive dripping. The rheology modifier may be a film former or may act cooperatively with a film forming agent to form a barrier that provides additional protection.

Preferred rheology modifiers include colloidal aluminum silicate, colloidal clays, polyvinyl pyrrolidone, polyvinyl acetate, polyvinyl alcohol, polyalkylene oxides, polyacrylamides, or mixtures thereof.

Water soluble or water dispersible rheology modifiers that are useful can be classified as inorganic or organic. The organic thickeners can further be divided into natural synthetic polymers with the latter still further subdivided into synthetic natural-based synthetic petroleum-based.

Organic thickeners are generally compounds such as colloidal magnesium aluminum silicate (Veegum), colloidal clays (Bentonites), or silicas (Cab-O-Sils) which have been fumed to create particles with large surface size ratios.

Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are salts of complex anionic polysaccharides. Synthetic natural-based thickeners having application are cellulosic derivatives wherein the free hydroxyl groups on the linear anhydro-glucose polymers have etherified or esterified to give a family of substances which dissolve in water and give viscous solutions. This group of materials includes the alkyl and hydroxyalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

Surfactants

The composition may optionally include a surfactant to help with detergency, surface wetting, and antimicrobial performance. Suitable surfactants include nonionic surfactants, anionic surfactants, cationic surfactants, amphoteric surfactants, amine oxides, and the like.

Anionic surfactants suitable for use in the present compositions and methods include n-octanesulfonate, available as NAS 8D from Ecolab Inc., n-octyl dimethylamine oxide, n-decyl dimethyl amine oxide, cocoa dimethylamine oxide, and the commonly available aromatic sulfonates such as the alkyl benzene sulfonates (e.g. dodecylbenzene sulfonate, cumene sulfonate, xylene sulfonates) or naphthalene sulfonates. Most preferred anionic surfactants include $C_6$-$C_{24}$ alkylbenzene sulfonates, $C_6$-$C_{24}$ olefin sulfonates, $C_6$-$C_{24}$ paraffin sulfonates, cumene sulfonate, xylene sulfonate, $C_6$-$C_{24}$ alkyl naphthalene sulfonates, $C_6$-$C_{24}$ alkyl or dialkyl diphenyl ether sulfonates or disulfonates, $C_4$-$C_{24}$ mono or dialkyl sulfosuccinates, sulfonated or sulfated fatty acids, $C_6$-$C_{24}$ alcohol sulfates (preferably $C_6$-$C_{12}$ alcohol sulfates), $C_6$-$C_{24}$ alcohol ether sulfates having 1 to about 20 ethylene oxide groups, and $C_4$-$C_{24}$ alkyl, aryl or alkaryl phosphate esters or their alkoxylated analogs having 1 to about 40 ethylene, propylene or butylene oxide units, or mixtures thereof.

Additional suitable surfactants include nonionic surfactants of $C_6$-$C_{24}$ alcohol ethoxylates (preferably $C_6$-$C_{14}$ alcohol ethoxylates) having 1 to about 20 ethylene oxide groups (preferably about 9 to about 20 ethylene oxide groups); $C_6$-$C_{24}$ alkylphenol ethoxylates (preferably $C_8$-$C_{10}$ alkylphenol ethoxylates) having 1 to about 100 ethylene oxide groups (preferably about 12 to about 20 ethylene oxide groups); $C_6$-$C_{24}$ alkylpolyglycosides (preferably $C_6$-$C_{20}$ alkylpolyglycosides) having 1 to about 20 glycoside groups (preferably about 9 to about 20 glycoside groups); $C_6$-$C_{24}$ fatty acid ester ethoxylates, propoxylates or glycerides; and $C_4$-$C_{24}$ mono or dialkanolamides.

In addition, useful surfactants include those that perform a dual function. For example, surface active compounds such as mono, di and trialkyl phosphate esters may be added to the composition to aid in wetting, but also to suppress foam and provide some antimicrobial activity. Such phosphate esters would generally be produced from aliphatic linear alcohols, there being from 8 to 12 carbon atoms in the aliphatic portions of the alkyl phosphate esters. Nonionic surfactants, fatty acid salts, and silicone-based materials can be added to reduce foam formation herein. Such materials tend to enhance performance of the other components of the composition.

Highly preferred surfactants include food additive surfactants. Thus, the invention includes food grade, or naturally derived or food surface compatible, wetting and detersive agents, for example, linoleic acid, sorbitan esters, sugar esters, lecithins and ethoxylated lecithins, PEG alkylates, linear alkylbenzene sulfonates, stearyl citrate, alkyl naphthalene sulfonates, Pluronics, and various short-chain fatty acids.

Potentiators

The composition may optionally include a potentiator such as a terpenoid. Terpenoids are defined as materials with molecular structures containing carbon backbones made up of isoprene (2-methylbuta-1,3-diene) units. Isoprene contains five carbon atoms and therefore, the number of carbon atoms in any terpenoid is a multiple of five. It is believed that terpenoids assist in promoting the uptake of antimicrobial compounds and preservatives by cells of bacteria and fungi, thereby increasing the efficacy of the antimicrobial compound or preservative. See U.S. Pat. No. 6,319,958 and DE 195 23 320 which are incorporated by reference in their entirety. Some non-limiting examples of terpenoids include α-terpinene, cineole, citral, citronellal, citronellol, farnesol, geraniol, limonene, linalool, methone, nerolidol, terpineol, camphene, menthone, myrcene, nerol, tetrayhydrogeraniol, tetrahydrolinalool, apritone, and bisabolol. The terpenoid is preferably farnesol, nerolidol, bisabolol, or apritone.

Flavoring Aids, Fragrances and Dyes

The composition may include a flavoring aid for imparting a desired flavor to a food product or for masking an undesirable flavor. Some non-limiting examples of flavoring aids include marinades, tenderizers, and spices typically associated with food products.

The composition may also include a fragrance including natural and synthetic fragrances. Some non-limiting examples of fragrances include aldehydes, ketones, esters, essential oils, and the like.

Finally, the composition may include a dye. Some non-limiting examples of suitable dyes include FD&C and D&C dyes.

Food Product

As used herein, the term "food product" or "food" refers to any food or beverage item that may be consumed by humans or mammals. Some non-limiting examples of a "food product" or "food" include the following: meat products including ready-to-eat ("RTE") meat and poultry products, processed meat and poultry products, cooked meat and poultry products, and raw meat and poultry products including beef, pork, and poultry products; fish products including cooked and raw fish, shrimp, and shellfish; produce including whole or cut fruits and vegetables and cooked or raw fruits and vegetables; pizzas; ready made breads and bread doughs; cheese, eggs, and egg-based products; and pre-made food items such as pre-made sandwiches. The present invention is particularly useful for meat and poultry products. Specific examples of meat products including RTE deli or luncheon meats like turkey, ham, roast beef, hot dogs, and sausages. Additionally, the present invention can be used on bacon and pre-made, pre-assembled, or pre-packaged meals such as TV dinners and microwaveable entrees or meals.

Application of the Antimicrobial Composition

The antimicrobial composition may be applied to the food product prior to, after, or substantially simultaneously with the packaging of the food product. Alternatively, the composition may be applied to the food product without packaging.

The antimicrobial composition may be applied to the food product in several ways. In some embodiments, the antimicrobial composition may be applied directly to the food product in a number of ways including spraying, misting, rolling, and foaming the antimicrobial composition directly onto the food product and the like, and immersing the food product in the antimicrobial composition. The antimicrobial composition may be applied in an injection such as in an injection solution, or the antimicrobial composition may be applied as part of a marinade or tenderizer that is applied to the food product.

In some embodiments, the antimicrobial composition may be indirectly applied to the food product. The antimicrobial composition may be applied to the packaging prior to inserting the food product into the packaging or prior to applying the packaging to the food product. The antimicrobial composition then contacts the food product when the food product is packaged. As used herein, a "packaged food product" means a food product that has been placed in packaging but not yet sealed. The antimicrobial composition may be applied to the packaging after the food product has been inserted into the packaging or after applying the packaging to the food product (e.g., the antimicrobial composition may be squirted or otherwise introduced into the packaging after the food has been placed in the packaging but prior to sealing the packaging). The antimicrobial composition may be applied to the food product substantially simultaneously with the packaging of the food product. Additionally, food packaging or food casing (e.g., hot dog or sausage casing) may be coated, treated, or impregnated with the antimicrobial composition, and the antimicrobial composition is applied to the food product when the food product is placed inside the packaging or casing.

Examples of preferred methods of use are described in greater detail in the co-pending application entitled, ANTIMICROBIAL COMPOSITIONS AND METHODS FOR TREATING PACKAGED FOOD PRODUCTS, filed concurrently herewith with Ser. No. 11/459,067, the entire disclosure of which is incorporated by reference herein.

For a more complete understanding of the invention, the following examples are given to illustrate some embodiment. These examples and experiments are to be understood as illustrative and not limiting. All parts are by weight, except where it is contrarily indicated.

EXAMPLES

Example 1

The following is an example of an octanoic acid composition used in the method of the present invention where the octanoic acid composition is activated by passage of the food product through a simulated shrink tunnel.

For this example, a solution of 1,000 ppm to about 10,000 ppm octanoic acid, from about 1.0% to about 4.0% ethylene oxide/propylene oxide co-polymer (Pluronic F108), and about 2.0 to about to about 6.0% propylene glycol is adjusted to pH 1.0 with any GRAS acid such as phosphoric acid.

TABLE 1

Octanoic Acid Composition

| Level (Wt. %) | Raw Material |
|---|---|
| 88.15 | Water |
| 2.85 | Pluronic F108 |
| 5.00 | Propylene Glycol |
| 3.00 | Phosphoric Acid (75%) |
| 1.00 | Octanoic Acid |

Final Solution pH~1.18

An equal-part mixture of five strains of *L. monocytogenes* including ATCC 19112, ATCC 19114, ATCC 19115, ATCC 7644, and NCTC 10890 suspended in phosphate buffered dilution water was used as the inoculum. 0.1 milliliters of the inoculum was placed onto a RTE turkey breast, spread with a sterile bent glass rod, followed by storage at 5° C. for 10 minutes to allow for bacterial attachment. RTE turkey breasts were then sprayed with the antimicrobial composition described in Table 1 for 15 seconds. In this example, the volume of the antimicrobial composition applied to each RTE turkey breast was about 15 milliliters. The turkey breasts were placed in bags. The bags were immediately vacuum-packaged, and submerged in 200° F. water for 15 seconds to simulate passage through a shrink tunnel. The bags were then submerged in a 2° C. water bath for ≧1 minute. Two replicates were completed per treatment. The samples were stored at 5° C. for 24 hours before being analyzed for populations of *L. monocytogenes*. Fifty milliliters of University of Vermont broth were added to each bag. The RTE turkey breasts were tumbled to recover cells. The resulting suspension was plated in Modified Oxford Medium Agar and the plates were incubated at 35° C. for 72 hours prior to enumeration of *L. monocytogenes*.

TABLE 2

Efficacy of Octanoic Acid and Heat on *L. monocytogenes* on RTE Turkey

| Treatment | Heat Exposure (sec) | Average Log$_{10}$ CFU/sample | Average Log$_{10}$ Reduction |
|---|---|---|---|
| Water | 0 | 7.61 | NA |
| 1% Octanoic Acid | 0 | 6.41 | 1.20 |
|  | 15 | 5.57 | 2.04 |

Following treatment with 1% octanoic acid, a 1.20 log reduction of *L. monocytogenes* resulted. However, the activation of octanoic acid reduced *L. monocytogenes* populations by 2.04 logs within the food product. It has been published that naturally occurring *L. monocytogenes* contamination levels in RTE meat products is generally low (about <1 CFU/g). Gombas, D. E., et al. (2003). Survey of *Listeria monocytogenes* in Ready-to-Eat Foods. *Journal of Food Protection* (66). 559-569. Thus, once activated, the antimicrobial composition in Example 1 renders the RTE product essentially free of *Listeria monocytogenes* contamination. These results show that octanoic acid meets FSIS requirements of a post-lethality treatment as described in FSIS Form 10,240-1.

Example 2

The following example determined the efficacy of 1.0% octanoic acid at reducing *L. monocytogenes* on RTE oven roasted turkey breasts where the octanoic acid was activated by simulating passage of the food product through a simulated immersion shrink tunnel. For this example a solution of 1% octanoic acid using 3% Polysorbate 20 as a coupler was prepared and acidified using 2.55% citric acid. Four test solutions were prepared and each pH adjusted to a different pH from pH 2 to pH 5 using up to 1.08% sodium hydroxide. An equal-part mixture of five strains of *L. monocytogenes*, including ATCC 19112, ATCC 19114, ATCC 19115, ATCC 7644, and NCTC 10890, suspended in a phosphate buffered dilution water, was used as the inoculum. Sample surfaces were spot-inoculated with 50 microliters of the inoculum. The inoculum was spread using a sterile bent glass rod. Inoculated samples were stored at 5° C. for 30 minutes before treatment to allow for bacterial attachment. The inoculated turkey samples were transferred to shrink bags. Fifteen milliliters of the octanoic acid formula were added to bags which were immediately vacuum-packaged and submerged in water heated to 200° F. for 10 seconds (treated samples) or 2 seconds (untreated control samples). Three replicates were completed per treatment. The samples were stored at 5° C. for 2 hours and 21 days before analyzed for populations of *L. monocytogenes*. Fifty milliliters of University of Vermont broth were added to each bag. The turkey samples were tumbled for 50 rotations and the resulting suspension was plated in Modified Oxford Medium Agar. Plates were incubated at 35° C. for 48 hours before the pathogen was enumerated.

TABLE 3

Efficacy of 1.0% Octanoic Acid Acidified with Citric Acid
on *L. monocytogenes* on RTE Oven Roasted Turkey Breasts

| Treatment Solution | Average $Log_{10}$ CFU/sample At 2 Hours | $Log_{10}$ Reduction Vs. Control At 2 Hours | Average $Log_{10}$ CFU/sample At 21 Days | $Log_{10}$ Reduction Vs. Control At 21 Days |
| --- | --- | --- | --- | --- |
| Untreated Control | 4.93 | Not Applicable | 8.68 | Not Applicable |
| 1.0% Octanoic Acid @ pH 2 | 2.28 | 2.65 | 2.48 | 6.20 |
| 1.0% Octanoic Acid @ pH 3 | 2.46 | 2.47 | 3.79 | 4.89 |
| 1.0% Octanoic Acid @ pH 4 | 2.13 | 2.80 | 3.94 | 4.74 |
| 1.0% Octanoic Acid @ pH 5 | 2.46 | 2.47 | 3.91 | 4.77 |

The treatment of the oven roasted turkey breasts with 1.0% octanoic acid resulted in a >2.4 log reduction of *L. monocytogenes* at 2 hours and >4.7 log reduction of *L. monocytogenes* after 21 days of storage. Therefore, once activated, the antimicrobial compositions substantially suppress the growth of *L. monocytogenes* on treated RTE foods. It has been published that naturally occurring *L. monocytogenes* contamination levels in RTE meat products is generally low (about <1 CFU/g). Thus, once activated, the antimicrobial composition renders the RTE product essentially free of *Listeria monocytogenes* contamination. This example shows that the use of octanoic acid meets FSIS requirements of a post-lethality treatment as described in FSIS Form 10,240-1, and may meet the requirements of an antimicrobial agent or process which suppresses the growth of *L. monocytogenes* as described in FSIS Form 10,240-1.

Example 3

The following example determined the efficacy of an octanoic acid solution at killing *Listeria monocytogenes* on turkey frankfurters when used in the method of the present invention where the octanoic acid composition was activated by simulating passage of the food product through a simulated immersion shrink tunnel.

For this example, solutions of 990, 5,000 and 10,000 ppm octanoic acid using sodium 1-octanesulfonate as a coupler were prepared and acidified using phosphoric acid. The 10,000 ppm octanoic acid solution was made with 1% octanoic, 1% 1-hydroxyethylidene-1,1-diphosphonic acid, 1.25% sodium 1-octanesulfonate, and was acidified to pH 1.2 using phosphoric acid. The 5,000 ppm octanoic acid solution was made using a 50% of the 10,000 ppm octanoic acid, 50% water and a pH of 1.4. The 990 ppm octanoic acid solution was made with 9.9% of the 10,000 ppm octanoic acid, 89.42% water and brought to pH 1.5 with 0.68% phosphoric acid. An equal-part mixture of five strains of *L. monocytogenes* including ATCC 19112, ATCC 19114, ATCC 19115, ATCC 7644, and NCTC 10890, suspended in phosphate buffered dilution water, was used as the inoculum. 0.125 milliliters of the inoculum was pipetted onto each turkey frankfurter within a sterile polyethylene bag. The frankfurters were stored at 10° C. for 10 minutes to allow for bacteria attachment. 1 milliliter of the designated octanoic acid formula (or sterile water for the control) was added to each bag. Bags were vacuum-packaged, and submerged in 200° F. water for 15 seconds to simulate passage through an immersion shrink tunnel. The bags were then submerged in a 2° C. water bath for >1 minute. Three replicates were completed per treatment. The samples were stored at 5° C. for 24 hours before analyzed for populations of *L. monocytogenes*. Fifteen milliliters of University of Vermont broth were added to each bag. The frankfurters were massaged for 1 minute to recover cells. The resulting suspension was plated in Modified Oxford Medium Agar and the plates were incubated at 35° C. for 72 hours prior to enumeration of *L. monocytogenes*.

TABLE 4

Efficacy of 990, 5,000 and 10,000 ppm Octanoic Acid
in Killing *L. monocytogenes* on Turkey Frankfurters

| Treatment Solution | Heat Exposure (sec) | Average $Log_{10}$ CFU/sample | $Log_{10}$ Reduction Vs. Control |
| --- | --- | --- | --- |
| Water (control) | 15 Sec @ 200 F. | 5.25 | Not Applicable |
| 990 ppm Octanoic Acid | 15 Sec @ 200 F. | 4.56 | 0.69 |
| 5,000 ppm Octanoic Acid | 15 Sec @ 200 F. | 3.90 | 1.35 |
| 10,000 ppm Octanoic Acid | 15 Sec @ 200 F. | 2.59 | 2.66 |

The treatment of turkey frankfurters with 10,000 ppm octanoic acid with heat activation resulted in a 2.66 log reduction of *L. monocytogenes*. It has been published that naturally occurring *L. monocytogenes* contamination levels in RTE meat products is generally low (about <1 CFU/g). Thus, once activated, the antimicrobial composition renders the RTE product essentially free of *Listeria monocytogenes* contamination. This example shows again that octanoic acid meets FSIS requirements of a post-lethality treatment as described in FSIS Form 10,240-1.

Example 4

The following example determined the efficacy of a 1.0% octanoic acid solution against *L. monocytogenes* on roast beef.

For this example, a solution of 1% octanoic acid using 3% Polysorbate 20 as a coupler was prepared and acidified to pH 2.0 using 0.3% phosphoric acid. A second solution of 1% octanoic acid using 3% Polysorbate 20 as a coupler was prepared which was brought to pH 4.0 using 2.55% citric acid and 0.6% sodium hydroxide. The efficacy of both formulas was evaluated. An equal-part mixture of five strains of *L. monocytogenes*, including Scott A (serotype 4b, human isolate), H7750 (not serotyped, frankfurter isolate), AC33 (not serotyped, cooked ham isolate), LM108M (serotype 1/2b, salami isolate), and F6854 (serotype 1/2a, frankfurter isolate), suspended in phosphate buffered dilution water were used. Roast beef samples were spot-inoculated with 50 microliters of the inoculum. The inoculum was spread using a sterile bent glass rod. Inoculated RTE food product samples were stored at 5° C. for 30 minutes before treatment to allow for bacterial attachment. RTE food product samples were placed in shrink bags. The RTE food product samples were treated with octanoic acid via a direct application of about 15 milliliters of either octanoic acid formula to each treated sample. The bags were immediately vacuum-packaged with a 2-second submersion in water heated to 200° F. Three replicates were completed per treatment. Samples were stored at 5° C. for 24 hours before being analyzed for population of *L. monocytogenes*. Fifty milliliters of University of Vermont broth were added to each bag. RTE food product samples were tumbled for 50 rotations and the resulting suspension was plated in Modified Oxford Medium Agar. Plates were incubated at 35° C. for 48 hours before the pathogen was enumerated.

TABLE 5

Efficacy of 1% Octanoic Acid and Heat in Killing *L. monocytogenes* on Roast Beef

| Antimicrobial Treatment | Heat | Average $\text{Log}_{10}$ CFU/sample | $\text{Log}_{10}$ Reduction Vs. Control |
|---|---|---|---|
| None (control) | 2 sec | 4.31 | NA |
| 1% Octanoic Acid acidified to pH 2 with phosphoric acid | 2 sec | 3.13 | 1.18 |
| 1% Octanoic Acid acidified to pH 4 with citric acid | 2 sec | 2.22 | 2.09 |

Treatment of roast beef with 1% octanoic acid acidified to pH 2 with phosphoric acid and heat resulted in a 1.18 log reduction of *L. monocytogenes*. Treatment of roast beef with 1% octanoic acid acidified to pH 4 with citric acid and heat resulted in a 2.09 log reduction of *L. monocytogenes*. It has been published that naturally occurring *L. monocytogenes* contamination levels in RTE meat products is generally low (about <1 CFU/g). Thus, the antimicrobial composition renders the RTE product essentially free of *Listeria monocytogenes* contamination. This example shows that octanoic acid meets FSIS requirements of a post-lethality treatment as described in FSIS Form 10,240-1.

The foregoing summary, detailed description, and examples provide a sound basis for understanding the invention, and some specific example embodiments of the invention. Since the invention can comprise a variety of embodiments, the above information is not intended to be limiting. The invention resides in the claims.

What is claimed is:

1. A ready to use antimicrobial composition for application on a ready-to-eat meat or poultry product consisting of:
   (a) about 0.1 wt.% to about 5 wt.% octanoic acid;
   (b) an acidulant selected from the group consisting of a citric acid, phosphoric acid and mixtures thereof;
   (c) a buffer selected from the group consisting of a citrate salt, a phosphate salt and a mixture thereof;
   (d) about 0.05 wt.% to about 10 wt.% of a mixture of a sorbitan ester and an alkyl polyglucoside; and
   (e) a carrier selected from the group consisting of water, propylene glycol, and mixtures thereof;
   wherein the composition includes only materials considered GRAS or food additive ingredients and the composition is adapted to remain on the food product after the food product is packaged and exposed to activation energy that activates the antimicrobial composition.

2. The composition of claim 1, wherein the octanoic acid is an ester or salt of octanoic acid.

3. The composition of claim 1, wherein the composition is a concentrate composition.

4. The composition of claim 1, wherein the composition is a ready-to-use composition.

5. A ready to use antimicrobial composition for application on a food product consisting of:
   (a) about 0.1 wt.% to about 5 wt.% octanoic acid;
   (b) an acidulant selected from the group consisting of a citric acid, phosphoric acid and mixtures thereof;
   (c) buffer selected from the group consisting of a citrate salt, a phosphate salt and a mixture thereof; and
   (d) about 0.05 wt.% to about 10 wt.% of a sorbitan ester and an alkyl polyglucoside; and
   (e) a carrier selected from the group consisting of water, propylene glycol, and mixtures thereof;
   wherein the composition includes only materials that are considered GRAS or food additive ingredients.

6. The composition of claim 5, wherein the octanoic acid is an ester or salt of octanoic acid.

7. The composition of claim 5, wherein the composition is a concentrate composition.

8. The composition of claim 5, wherein the composition is a ready-to-use composition.

* * * * *